(12) United States Patent
Yoo et al.

(10) Patent No.: US 7,433,505 B2
(45) Date of Patent: Oct. 7, 2008

(54) METHOD OF DENTAL MICROSCOPIC PROCEDURE

(76) Inventors: Ben Yoo, 986 Calle La Primavera, Glendale, CA (US) 91208; Young Han, 3719 First St., La Crescenta, CA (US) 91214; Sung Shim, 220 S. Gale Dr., #9, Beverly Hills, CA (US) 90211; Won Joo Woo, 23132 Rio Lobos Rd., Diamond Bar, CA (US) 91765

( * ) Notice: Subject to any disclaimer, the term of this patent is extended or adjusted under 35 U.S.C. 154(b) by 585 days.

(21) Appl. No.: 11/263,817

(22) Filed: Nov. 1, 2005

(65) Prior Publication Data

US 2007/0098237 A1 May 3, 2007

(51) Int. Cl.
*G06K 9/00* (2006.01)
*A61B 6/14* (2006.01)

(52) U.S. Cl. ............... 382/128; 378/38; 378/168
(58) Field of Classification Search ......... 382/128–134; 378/38, 168, 191; 601/162
See application file for complete search history.

(56) References Cited

U.S. PATENT DOCUMENTS

| | | | |
|---|---|---|---|
| 6,093,019 A * | 7/2000 | Morandi et al. ............ 433/29 |
| 6,190,309 B1 | 2/2001 | Ooshima et al. | |
| 6,633,328 B1 | 10/2003 | Byrd et al. | |
| 6,754,279 B2 | 6/2004 | Zhou et al. | |
| 2003/0058989 A1 * | 3/2003 | Rotondo et al. ............ 378/40 |

* cited by examiner

*Primary Examiner*—Samir A Ahmed
*Assistant Examiner*—Mehdi Rashidian
(74) *Attorney, Agent, or Firm*—Park Law Firm; John K. Park (57) ABSTRACT

A method of dental microscopic procedure, using a digital surgical scope, includes steps for selecting a function of the digital surgical scope to perform, obtaining the corresponding images from the image data taking device or the image data processing/storing device, processing the images by the image data processing/storing device, and displaying the images on the displays. The dental surgical procedure is done by seeing the images displayed on the screen. The digital surgical scope includes a microscope lens assembly for magnifying an optical image of an object and an in-line illumination device for illuminating the object along the same optical axis and from the same direction of the microscope lens assembly. The image data processing/storing device is for manipulating the image taken by the microscope lens assembly and the image data taking device.

1 Claim, 12 Drawing Sheets

METHOD OF DENTAL MICROSCOPIC PROCEDURE

BACKGROUND OF THE INVENTION

The present invention relates to a method of dental microscopic procedure, which enables dentists to perform dental procedures including surgery by seeing the images on a screen, and not looking into a small eyepiece.

Furthermore, this invention relates to a method of dental microscopic procedure, which makes recording and manipulating images obtained from the digital surgical microscope, an image data taking device more convenient.

Current variations of the microscope disrupt the surgery process and do little to improve the quality, efficiency, safety, and comfort of surgical procedures. Today, many dentists use microscopes, limiting mobility, and causing neck, shoulder, and eye strain. Other telescopic microscopes require the dentist to adjust and constantly focus the scope to get an adequate image, interfering with the process of surgery and lending unnecessary difficulties during the operation. Should the dentist or the patient move, or if the scope gets displaced, relocate the image, then the image becomes blurry and requires one to refocus.

The present invention will relieve the user of the constant need to refocus due to its broader range, and will rid the user of the physical challenges posed by the current market of microscopes such as: eye, neck, shoulder and back strain.

Additionally, the digital surgical scope (DSS) offers tools and devices to improve future dental procedures and surgeries. The digital surgical scope offers a magnified (combined optical and digital zoom) high quality display of the surgery, as it happens in real time; while the imaging software allows the recording of streaming video and capturing of snap shots during surgery.

Unlike prior microscopes, the digital surgical scope is all-inclusive, offering the previously unavailable convenience of its all-in-one combination which includes: patient management, image processing software, in-line light illumination assembly, video camera unit, computer and monitor.

In addition the digital surgical scope is also unique in that it is highly maneuverable. It can be moved in virtually any direction and/or angle, unlike traditional scopes that are much more limited in directional/angle maneuverability.

Also, the digital surgical scope uniquely offers a realistic depth of field. Currently, available microscopes with attached video camera can only display a limited depth of field; thus making the practice of dentistry with the traditional microscope much more difficult. The depth of field of the digital surgical scope allows the dentist to see better while performing more difficult operations.

The digital surgical scope method is unique in that it offers digital enhancement to the image, allowing for much greater magnification than traditional scopes. For instance, 120× (combining optical and digital zoom) versus a maximum of 40× with traditional scopes.

The imaging software allows the user to record images either in a streaming video or photo snapshot directly to the patient's database. No other equipment sold today allows this function.

The dentist need not peer into a scope to perform procedures; instead, he/she can sit comfortably and view his/her work with more magnification on a monitor. He/she can also share this view with the patient or staff.

A split screen allows one to view various types of images including: photos and streaming video, simultaneously.

Traditional equipment limits the dentist. With a loupe and headlight he/she is tethered to the cord by the headlamp, resulting in poor ergonomics.

According to a published study, "80% of dentists suffer from chronic back and neck pain." The digital surgical scope will relieve the dentist from neck, back, and eye strain by allowing him/her to sit upright and giving more freedom to move. No other dental microscopic device on the market today can make that claim.

Accordingly, a need for a digital surgical scope has been present for a long time. This invention is directed to solve these problems and satisfy the long-felt need.

SUMMARY OF THE INVENTION

The present invention contrives to solve the disadvantages of the prior art.

An object of the invention is to provide a method of dental microscopic procedure, which enables dentists to perform dental procedures including surgery by seeing the live images on a screen and not looking into a small eyepiece.

Another object of the invention is to provide a method of dental microscopic procedure, which makes recording and manipulating the images obtained from the microscope and X-ray convenient.

The invention provides a method of dental microscopic procedure, which utilizes a digital surgical scope including in-line lens with in-line illumination assembly.

A method of dental microscopic procedure using a digital surgical scope includes steps for: selecting a function of the digital surgical scope to perform, obtaining the corresponding live or still images from the image data taking device or the live or still image data processing/storing device, processing the live or still images by the image data processing/storing device, and displaying the live or still images on the displays.

The dental surgical procedure is done by seeing the live or still images displayed on the display.

The digital surgical scope includes a digital surgical microscope, an image data taking device, an image data processing/storing device, and one or more displays for displaying the live or still image from the image data processing device.

The digital surgical scope includes a microscope lens assembly for magnifying an optical live image of an object, and an in-line illumination device for illuminating the object along the same optical axis from the same direction of the microscope lens assembly.

The purpose for the image data processing/storing device is to store and manipulate the image taken by the microscope lens assembly and the image data taking device.

The function of the digital surgical scope includes: capturing still images, streaming video images, enhancing images, replaying video images, browsing the history, and panning window. The process of capturing images includes: adjusting the quality of the image, capturing the adjusted image, and replaying the image until another function is executed. The captured image is stored in the image data processing/storing device.

The quality of the image includes: white balance, RGB color/Gamma value, viewing area, zoom in/out, and full screen display. The quality is also adjusted by controlling the gain, offset, and exposure of the image data taking device. The process of capturing the adjusted image includes steps of capturing a snap image or a video. The process of capturing the adjusted image includes steps of deleting the image, saving the image, and refreshing the image. The process of enhancing images includes steps of adjusting the quality of the image, analyzing the image, and annotating the image.

The quality of the image includes: brightness and contrast, edge enhancement, and histogram contrast. The step of analyzing the images includes: steps to manipulate the image to rotate, zoom in/out, pan, magnify, and measure geometrical dimension of the image. The step of manipulating includes a step to control the amount of light to the digital surgical scope with an iris.

The process of annotating the image includes steps of adding text and geometrical objects, which include lines and shapes.

The process of browsing the history includes steps of showing all of the stored images in thumbnail format, showing the images taken from the image data taking device along with images imported from outside of the system, comparing between the images from the image data taking device and the images from outside of the system, and selecting and displaying images out of the stored or displayed multiple images. The image from outside of the system includes X-ray exam images. The process of browsing the history further includes steps of selecting one or more images from the multiple images stored in the image data processing/storing device and showing the selected images on the displays.

The process of panning window includes steps of displaying live video images on the window screen, locating an area from streaming live video image, manipulating the located window, and displaying the manipulated window screen. The live window screen and the manipulated window screen are displayed within the same display. The process of manipulating includes scanning, magnifying, and zooming in and out, and the step of locating includes steps of tracking a cursor of a predetermined geometrical shape and zooming inside the cursor.

The process of Panning Window indicates steps of displaying live video images on the window screen, locating an area of interest from a streaming live video screen, locating an area of interest from streaming live video image, manipulating the located window, and displaying the manipulated window screen. The Panning Window function allows a dentist to both magnify and scan an area without having to move, re-focus, and re-adjust the camera or patient. The Panning Window enables the dentist to easily scan a specific tooth, surrounding teeth, or gum line by using a mouse to drag the locator box, which indicates the selected area on the screen with a red outlined box, accordingly. The live and manipulated window screen is shown within the same display. By clicking on the Panning Window icon, the Panning Window will appear on the left side of the Capture Window. When the Panning Window appears, the Zoon In icon must be clicked. Once the image has been zoomed in, the dentist will be able to use the Panning Window to explore the patient's affected area by dragging the locator box within the Panning Window. The dentist can also use the mouse to move within the Panning Window to scan and magnify the activated area by the locator box.

The image data processing/storing device stores, manipulates, and displays the image data from the image data taking device for dental treatment and surgery. The digital surgical scope displays finest images from the substantial distance which allows him/her plenty of comfortable workspace to perform his/her procedures on the patient, and the digital surgical scope includes an articulating mechanical arm to maneuver the digital surgical scope three-dimensionally.

The method further includes steps of deleting the images, exporting the images, importing images from outside of the system, multi-viewing, printing the images, and managing the images with a database, wherein the database is organized according to the patients.

The system further includes a plurality of digital surgical scopes, a communication network, and one or more controls for controlling the behavior of the image data processing/storing device. Also, a detachable mirror or a reflecting mechanism material such as a prism, disposed on a extended bar from the digital surgical scope for reflecting images from the inside of mouth to the digital surgical scope. The control includes a button, a pedal, and a lever. The method further includes steps of displaying the images on one or more remote displays, streaming and broadcasting the video images through the communication network via internet, and controlling the behavior of the image data taking device and the image data processing/storing device with the controls.

The image data taking device includes a charge coupled device (CCD) or a complementary metal-oxide-semiconductor (CMOS). The image data processing/storing device includes a computer.

The in-line illumination device includes a light source, and a beam splitter, and the light source includes a fiber optic device and emits light parallel to the optical axis of the microscope.

The mirror or prism changes the direction of the light from the light source by ninety (90) degrees or different angles. Also, the light source may emit directly to the beam splitter without a mirror or prism. The beam splitter is disposed in the optical axis of the microscope with forty five (45) or ninety (90) angles to the optical axis. The digital surgical scope further includes a main box, a fiber optic cable, and image data taking device.

The digital surgical scope has an adjustable magnification up to one hundred twenty (120) times including optical and digital zoom and could be higher in near future.

The method further includes steps of creating a database of information on a new patient and searching for information or an exam history on a predetermined patient from the database.

Alternatively, a dental microscopic procedure, using a digital surgical scope, includes steps for a) creating an entry in the database for a new patient; b) selecting a predetermined patient and retrieving the related information from the database; c) displaying the retrieved information; d) creating a new exam for the patient; e) opening the exam history and selecting an exam of the patient; f) capturing still images; g) enhancing images; h) storing streaming video images; i) browsing a history of the patient; and j) selecting and performing functions on the images, wherein the function includes deleting, exporting, importing, multi-viewing, printing, and managing the images with the database.

The process of capturing still images and/or storing streaming video images includes: c1) adjusting live image quality by adjusting the camera controls, white balance, RGB color gamma value, viewing area, zoom in, zoom out, and full screen, wherein the camera control includes gain, offset, and exposure; c2) viewing the adjusted live image; c3) capturing a snapshot image and a video clip; c4) controlling the capturing with a foot pedal or a button; c5) replaying the captured image or video; and c6) viewing details of the image or video by selecting functions of deleting, saving, and refreshing.

The process of enhancing images includes: e1) adjusting the image quality by controlling brightness, contrast, edge enhancement, and histogram contrast; e2) analyzing the images to manipulate the image to rotate, zoom in, zoom out, pan, magnify, and measure geometrical dimension, wherein the geometrical dimension includes angles, lengths, distances between two points; and e3) annotating the image for adding text and geometrical objects, wherein the geometrical objects includes lines and shapes.

The process of browsing the history of patient includes b1) showing all images in thumbnail format; b2) showing the digital surgical microscope image and X-ray images; b3) showing the comparison of the digital surgical scope video image and the X-ray image; b4) comparing images by selecting multiple images and multi-viewing; and b5) presenting a case for patient by selecting multiple images to present a possible treatment plan or treatment result from previous problems.

The digital surgical scope utilizes the best digital technology to improve upon the microscope. The current invention allows for a digital camera, which is placed at a distance of 2~20 inches from the patient's mouth, to capture the streaming live video image of any dental procedures/surgery to be displayed on one or more monitors in high resolution with adjustable magnification, optical zoom and digital zoom combined, during the dental procedure and surgery. Dentists can record the streaming video images in the built-in hard drive, with the computer software database, or an optional external driver or a DVD recorder, for clinical charting, future referencing, training, documentation, or other uses. The streaming video can be displayed in multiple monitors in different locations/rooms and can be transmitted to a streaming video broadcast via the internet.

The invention includes the transfer of the image with the adjustable magnification and the display of the live/streaming intraoral image on the monitor during the dental procedure/surgery. The. camera head, can be kept outside of the mouth at least 2~20 inches away from the mouth.

The advantages of the present invention are: (1) the method and system of dental microscopic procedures does not require a dentist to peer into a stationary eyepiece of the microscope so the dentist can view the area of interest displayed on a screen in comfort; (2) the system of the invention magnifies the image many times more than traditional microscopes and loupes with the addition of digital enhancement; (3) with the system of the invention, the dentist does not have to refocus when the patient moves in the chair. The field of view is large that repositioning the area of interest, refocusing is not necessary. With traditional scopes and loupes, the field of view decreases with magnification, and work must cease while the dentist refocuses for each slight movement. Additionally, in order to focus on a different area of interest while zoomed in, the dentists must first zoom out, identify the area of interest, zoom back in, and refocus. By contrast, the system requires no extra steps, only minimal adjustment is needed; (4) the image processing and management software of the invention allows the dentist to take photos, or stream video, and save them directly to the patient's digital file, within the patient database. These files are saved on the included hard drive or an optional external drive, with almost no effort and no interruption in the procedure. With a click of the button, or foot pedal, the dentist saves the still image or the streaming video, whichever he chooses, or both, to the built-in computer or an optional external drive connected to the USB port or other method such as firewire and so on. No other scope available today can offer that feature which provides for better documentation of procedures and updating patient's charts; (5) the system is able to display the surgical scope images and X-ray images together, side-by-side, on a split screen, this provides for a better diagnostic tool; (6) the system has the capability of displaying streaming video or recorded images on multiple monitors at one time, which is highly advantageous in presentation or educational meetings; (7) the system improves the ergonomics greatly, which frees the dentists from prolonged physical strain. The dentist is freer in his movements and needs not bend over with the weight of loupes and headlights burdening him, causing him pain; (8) the system is highly mobile. Because the system has no eyepiece, the dentist can move the camera head virtually any angle or position that he/she wishes, even at the side of the patient's mouth, which is impossible with the traditional microscope; (9) the learning curve for the system is very short. The dentist does not have to become versed in microscopic techniques. The digital display of the image on a monitor and the clear and simple push button operation of the system make it simple for anyone to use; (10) the depth of field is unequalled in any other scope. The depth of field is absolutely necessary in dental procedures because the dentist needs an accurate representation of the dimensionality of the mouth in order to work accurately. Without depth of field the mouth appears to be a flat surface with no dimension. Analog scopes, that have a video camera attached, have no/or limited depth of field, making it difficult to perform almost any procedure that requires the dentist to discern the three-dimensional environment of the mouth; (11) the system is a digital microscope; (12) the system offers a digital microscope with an all-in-one package including image processing and management software, computer with hard drive for image and data storage, 17" LCD monitor, control panels, built-in motorized video camera; (13) the view of the camera can be adjusted without looking into an eyepiece, from a comfortable sitting position all viewing adjustments can be made with the click of a button; and (14) the field of view remains large even during high magnification, not losing sight of the larger picture.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE INVENTION

Figure 1:
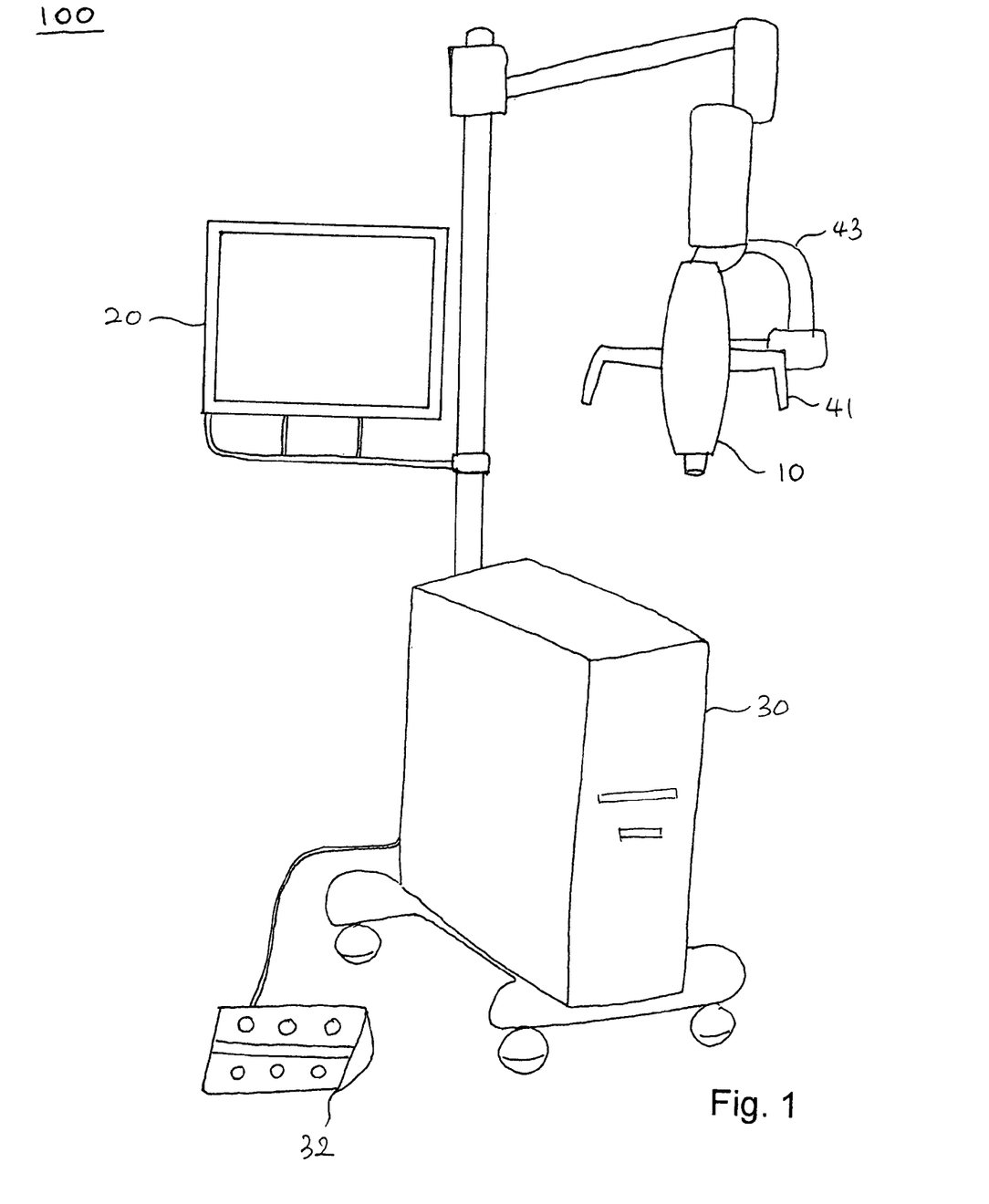
FIG. 1 is a perspective view of a digital surgical scope according to the present invention.

FIG. 1 shows a perspective view of a digital surgical scope 100 according to the present invention.

Figure 2:
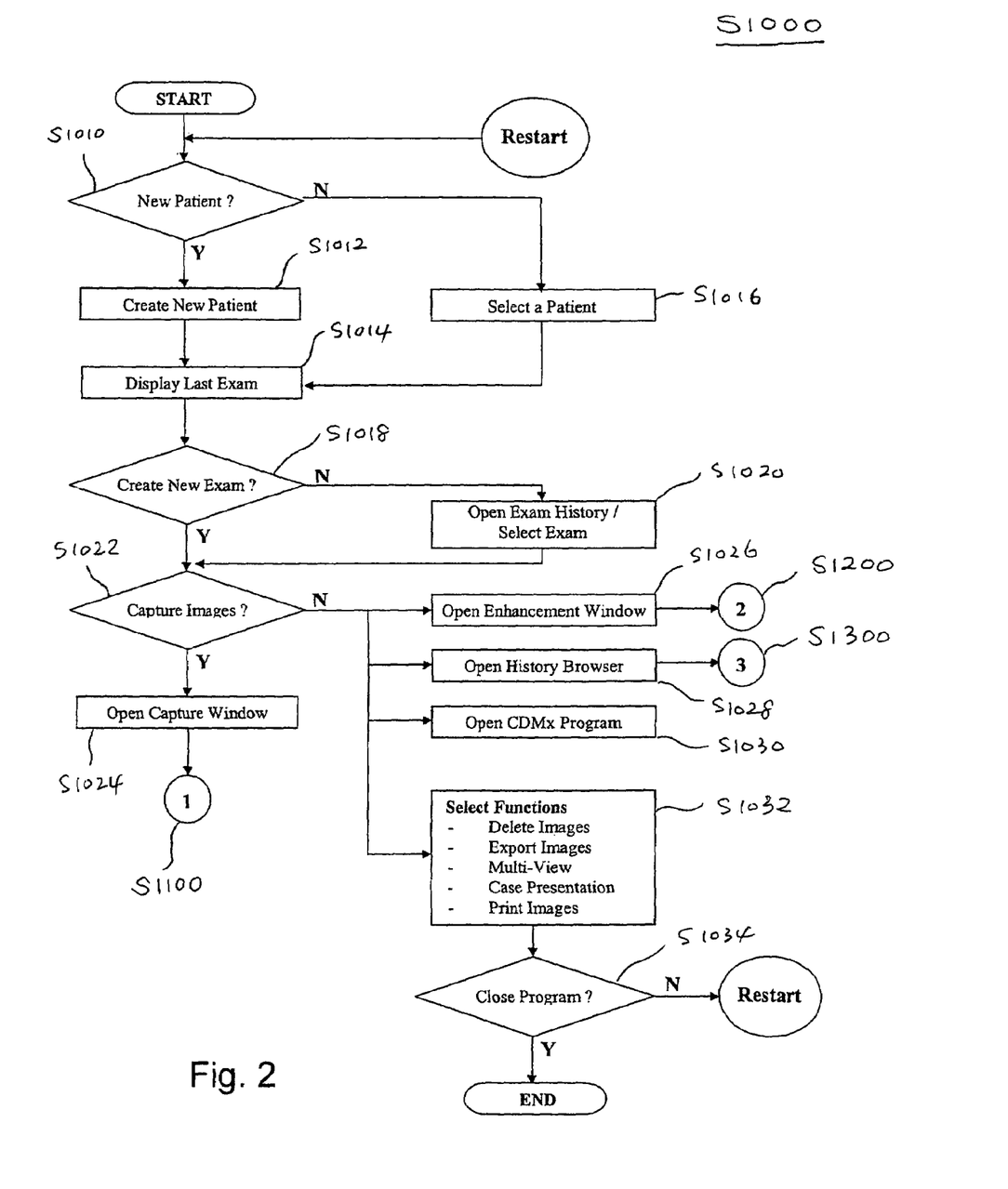
FIG. 2 is a flow chart showing a method of dental microscopic procedure according to the present invention.

FIG. 2 shows a flow chart showing a method S1000 of dental microscopic procedure according to the present invention.

The method S1000 of dental microscopic procedure, using a digital surgical scope 100, includes steps for selecting (S1022) a function of the digital surgical scope 100 to perform, obtaining (S1100) the corresponding images from the image data taking device 12 or the image data processing/storing device 30 (refer to FIGS. 1, 7, and 8), processing (S1200, S1300) the images by the image data processing/storing device 30, and displaying (S1014) the images on the displays 20 as shown in FIG. 1 and FIG. 2.

The dental surgical procedure is done by seeing the images displayed on the display 20.

The digital surgical scope 100 includes a digital surgical scope 10, an image data taking device 12, an image data processing/storing device 30, and one or more displays 20 for displaying the image from the image data processing device/storing 30.

Figure 7:
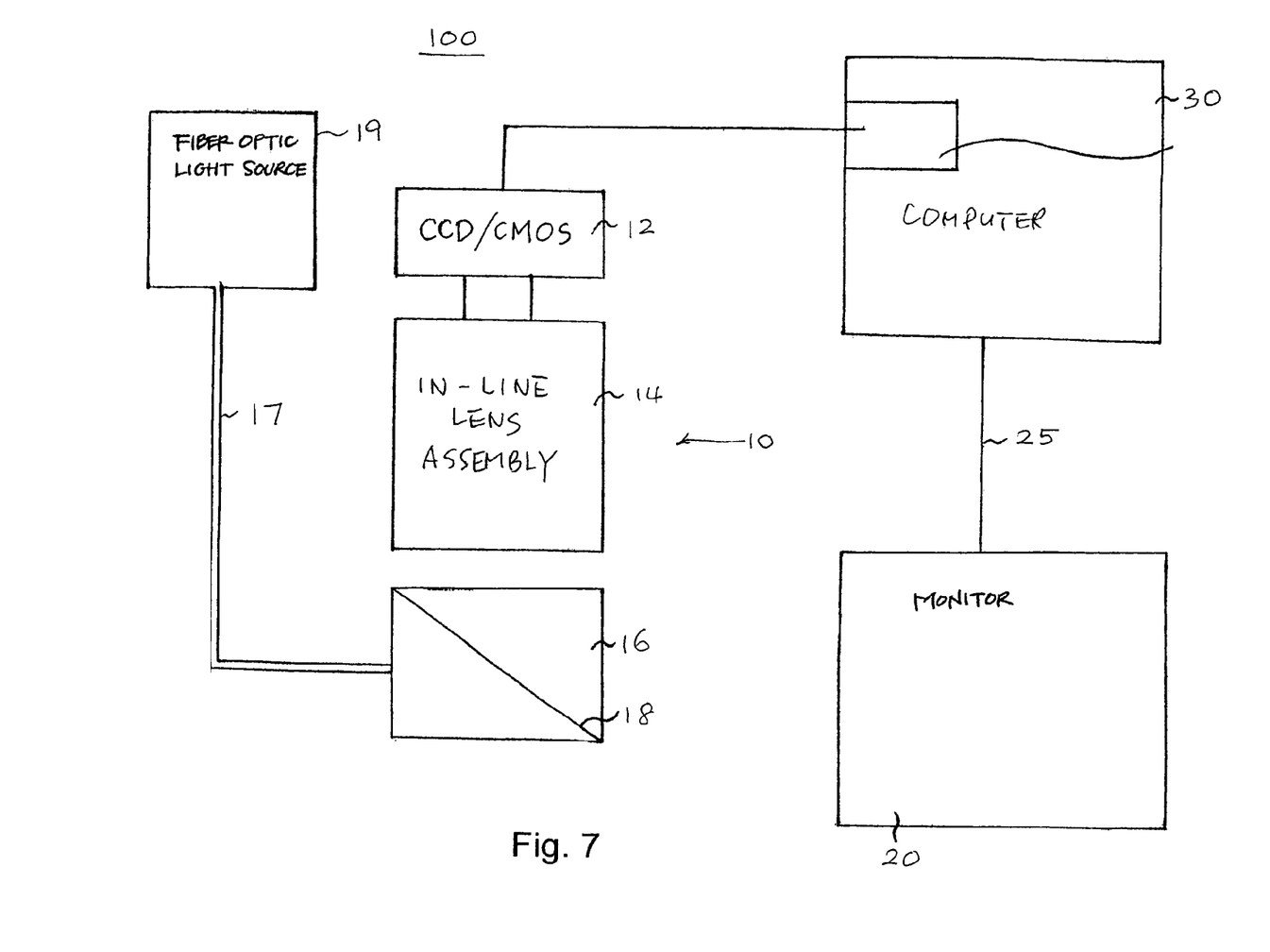
FIG. 7 is a block diagram of a digital surgical scope.
Figure 8:
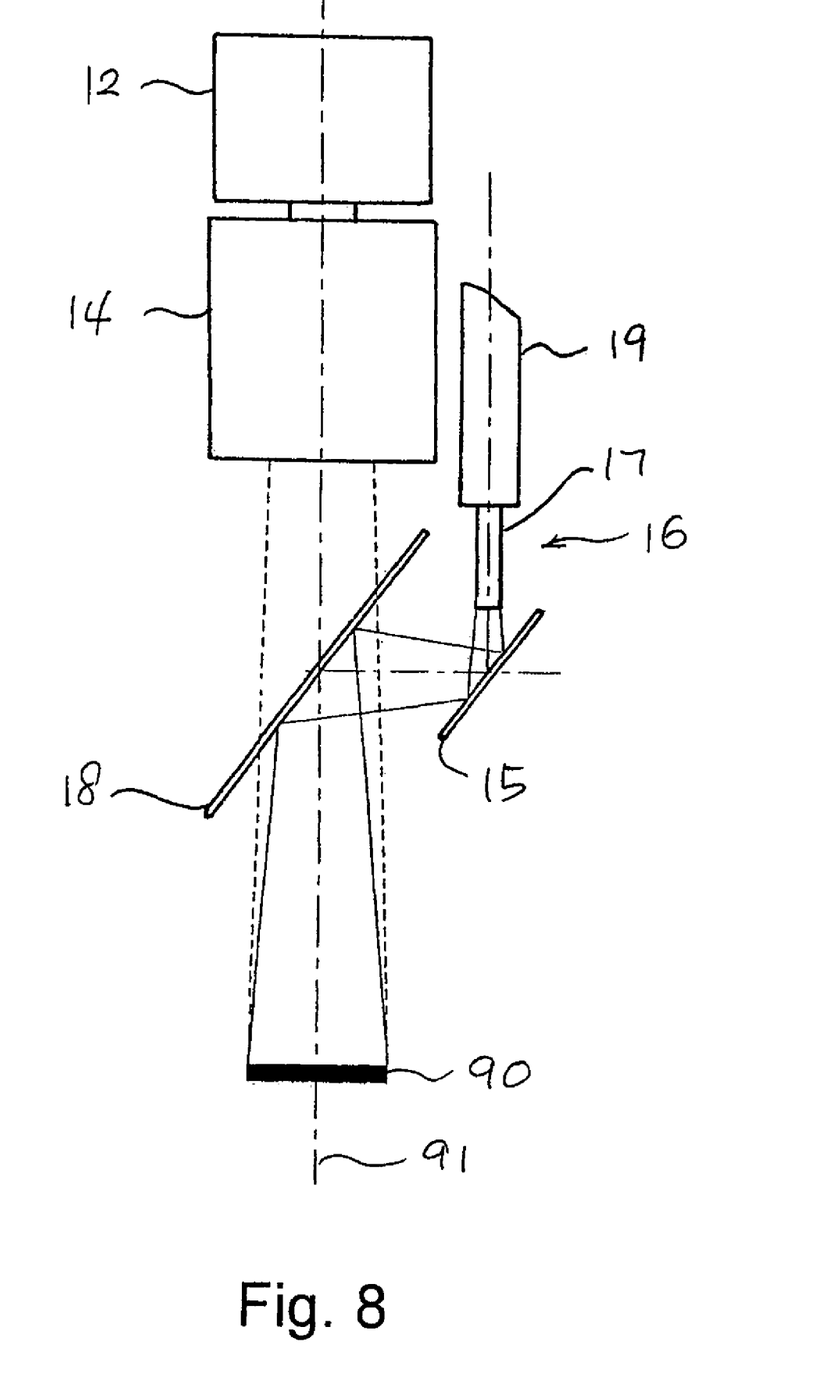
FIG. 8 is a front view of the digital surgical microscope.

As shown in FIG. 7 and FIG. 8, the digital surgical scope 10 includes a microscope lens assembly 14 for magnifying an optical image of an object 90 and an in-line illumination device 16 for illuminating the object 90 along the same optical axis 91 and from the same direction of the microscope lens assembly 14. The illumination device 16 includes a fiber optic light source 19, a beam splitter 18, and a fiber optic cable 17.

The image data processing/storing device 30 is for manipulating the image taken by the microscope lens assembly 14 and the image data taking device 12.

Figure 3:
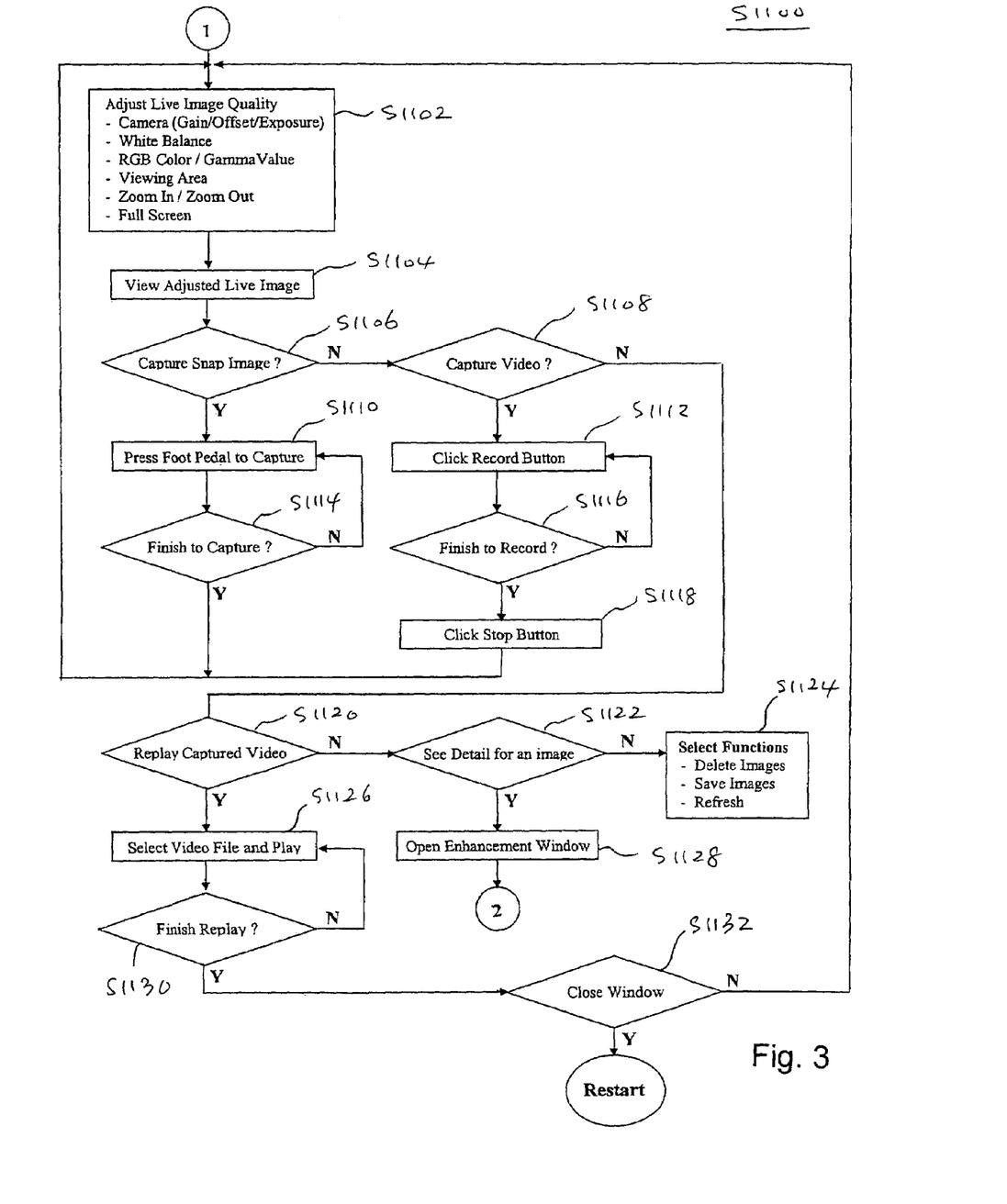
FIG. 3 is a flow chart showing a step of capturing images.
Figure 4:
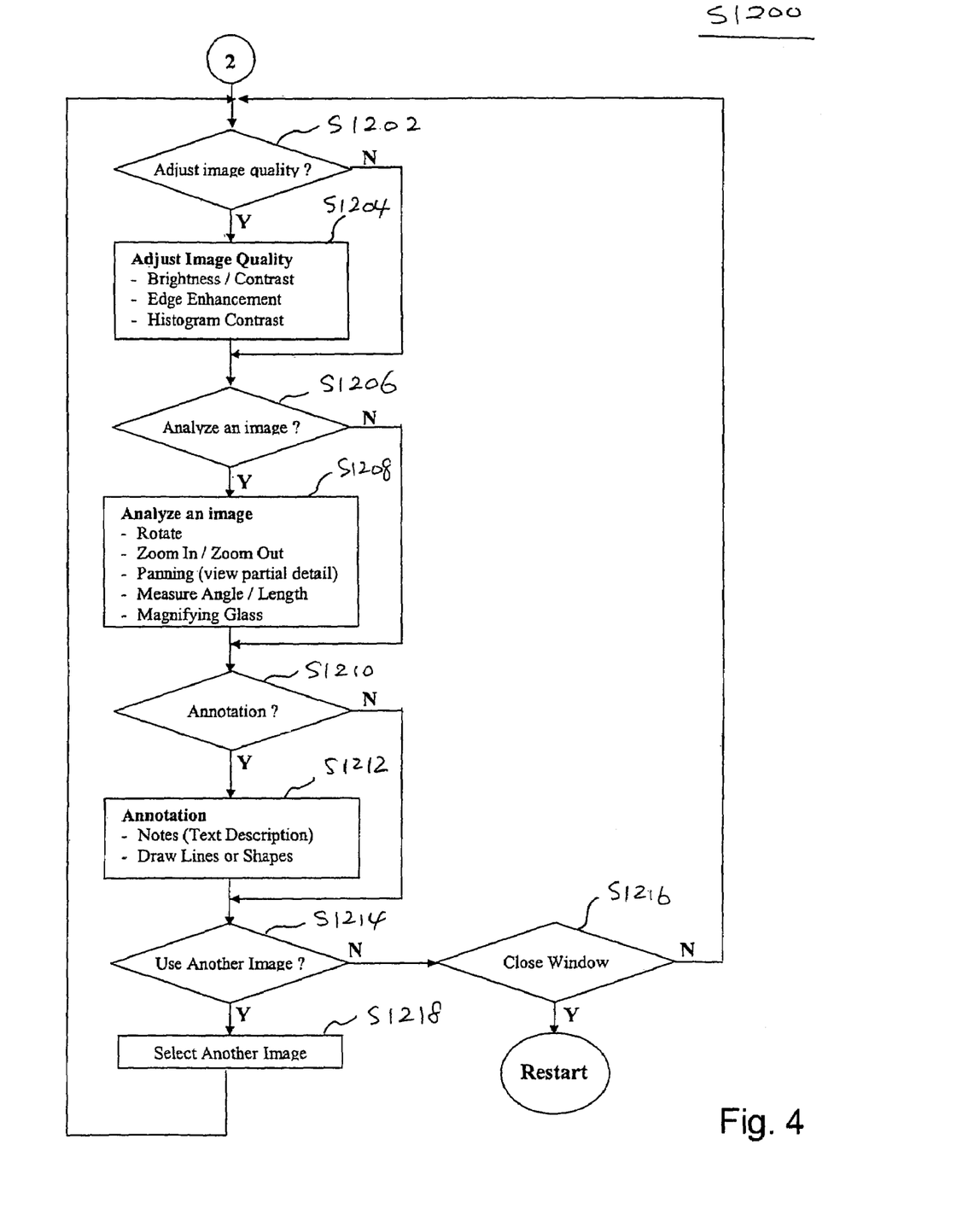
FIG. 4 is a flow chart showing a step of enhancing images.

The function of the digital surgical scope 100 includes capturing images S1100 (refer to FIG. 3), enhancing images S1200 (refer to FIG. 4), browsing the history S1300 (refer to FIG. 5), and panning window in S1208 (refer to FIG. 4). The step of capturing images S1100 includes steps of adjusting quality of the image S1102, capturing the adjusted images and video (S1106, S1110, S1114; S1108, S1112, S1116, S1118) and replaying the image (S1120, S1126, S1130) until another function is executed. The captured image is stored in the image data processing/storing device 30. The step of panning streaming video image on a window screen S1250 in S1208 is shown in detail in FIG. 6.

The quality of the image includes white balance, RGB color/Gamma value, viewing area, zoom in/out, and full screen. The quality is also adjusted by controlling the gain, offset, and exposure of the image data taking device 12. The step of capturing the adjusted image S1100 includes steps of capturing a snap image or a streaming video S1106, S1108. The step of capturing the adjusted image S1100 includes steps of deleting the image, saving the image, and refreshing the image S1124.

The step of enhancing images S1200 includes steps of adjusting quality of the image S1202, S1204, analyzing the image S1206, S1208, and annotating the image S1210, S1212. The quality of the image includes brightness and contrast, edge enhancement, and histogram contrast. The step of analyzing the images S1208 includes steps to manipulate the image to rotate, zoom in/out, pan, magnify, and measure geometrical dimension of the image. The step of manipulating includes a step to control the amount of light to the digital surgical scope with an iris that is in the fiber optic light source 19.

The step of annotating the image S1210 includes steps of adding text and geometrical objects, which includes lines and shapes.

Figure 5:
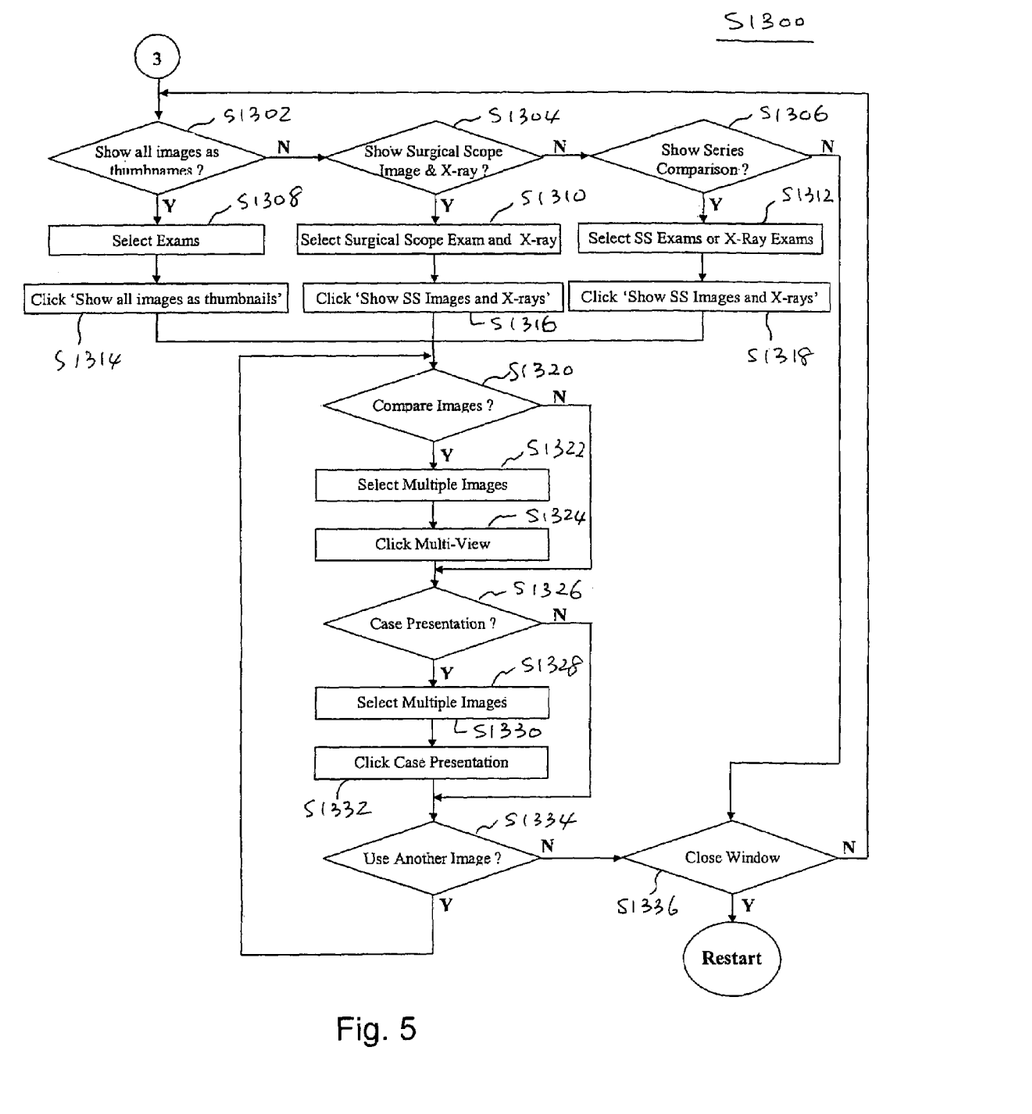
FIG. 5 is a flow chart showing a step of browsing history.

The step of browsing the history S1300 includes steps of showing all of the stored images in thumbnail format (S1302, S1308, S1314), showing the images taken from the image data taking device along with images imported from outside (S1304, S1310, S1316), comparing between the images from the image data taking device and the images from outside (S1306, S1312, S1318), and selecting and displaying images out of the stored or displayed multiple images (S1308, S1310, S1312). The image from outside of the system 100 includes X-ray exam images as in S1304, S1310, S1316, S1312, S1318.

The step of browsing the history S1300 further includes steps of selecting one or more images from the multiple images stored in the image data processing/storing device 30 (S1322, S1324) and showing the selected images on the displays 20 (S1332).

Figure 6:
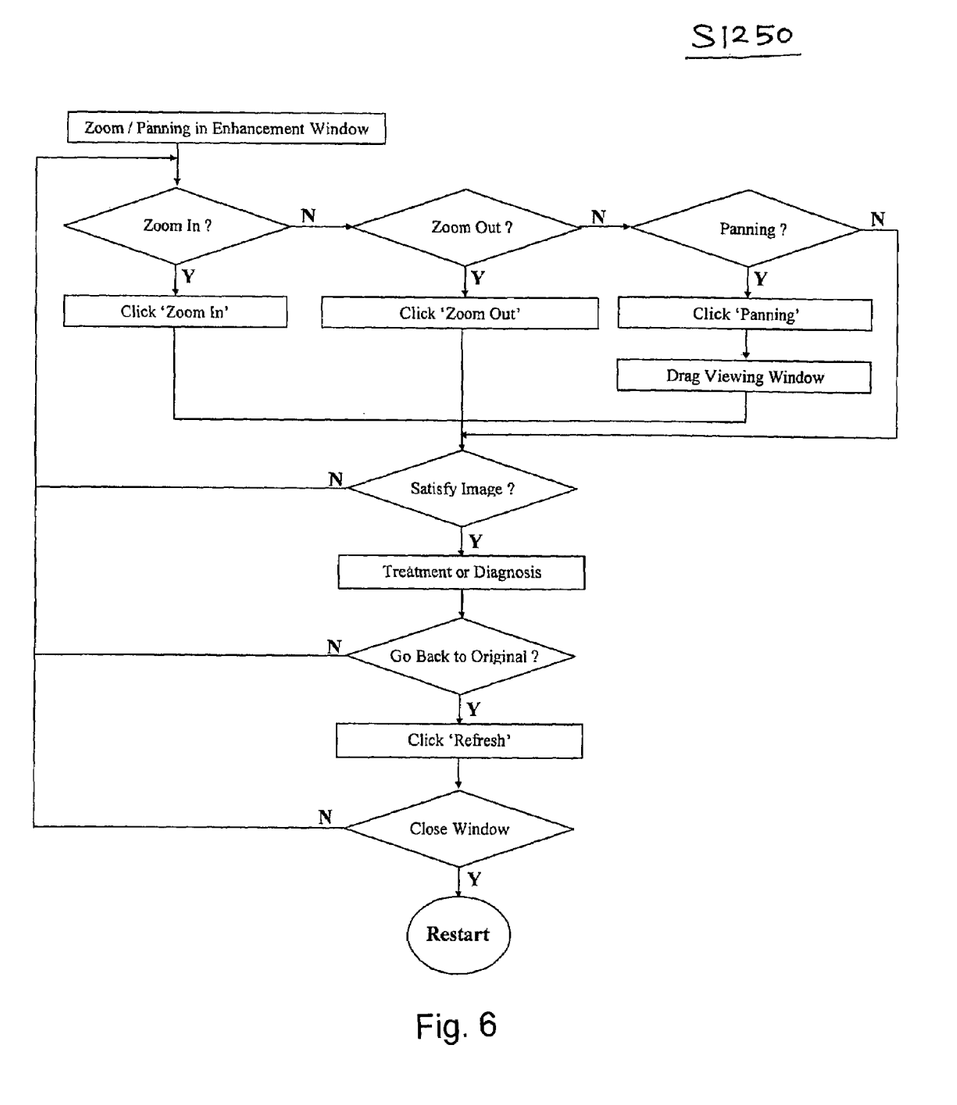
FIG. 6 is a flow chart showing a step of panning.

The process of panning window includes: displaying a live window screen, locating an area of interest from the live window screen, manipulating the located window, and displaying the manipulated window screen. The live window screen and the manipulated window screen are displayed on the same display 20. The process of manipulating includes: scanning, magnifying, and zooming in and out, and the process of locating includes tracking a cursor of a predetermined geometrical shape and zooming inside the cursor.

Figure 12:
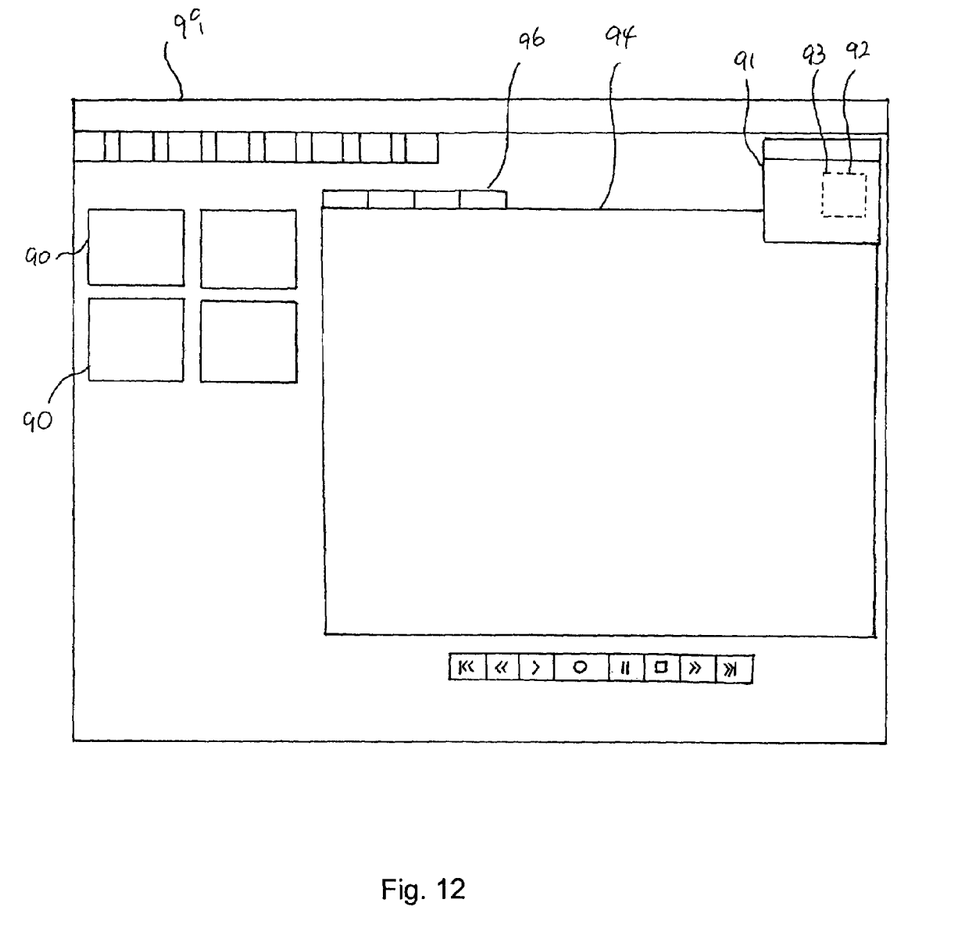
FIG. 12 is a screen shot showing the panning function.

As shown in FIG. 12, the process of Panning Window indicates steps of displaying live video images on the window screen 90, locating an area 91 of interest from a streaming live video screen 90, locating an area 92 of interest from streaming live video image 91, manipulating the located window 92, and displaying the manipulated window screen 94. The Panning Window function allows a dentist to both magnify and scan the area 94 without having to move, re-focus, and re-adjust the camera or patient using controls including the clickable controls 96. The Panning Window enables the dentist to easily scan a specific tooth, surrounding teeth, or gum line by using a mouse to drag the locator box 93, which indicates the selected area on the screen with a red outlined box, accordingly. The live and manipulated window screen is shown within the same display 99. By clicking on the Panning Window icon, the Panning Window will appear on the left side of the Capture Window. When the Panning Window appears, the Zoom In icon must be clicked. Once the image has been zoomed in, the dentist will be able to use the Panning Window to explore the patient's affected area by dragging the locator box within the Panning Window. The dentist can also use the mouse to move within the Panning Window to scan and magnify the activated area by the locator box.

The image data processing/storing device 30 stores, manipulates, and displays the image data from the image data taking device 12 for dental treatment and surgery. The digital surgical scope 100 is substantially detached from the patient, and the digital surgical scope 100 includes an articulating mechanical arm for maneuvering the digital surgical scope 10 three-dimensionally.

The method S1000 further includes steps (S1032) of deleting the images, exporting the images, importing images from outside of the system 100, multi-viewing, printing the images, and managing the images with a database, and the database is organized according to patients.

Figure 9:
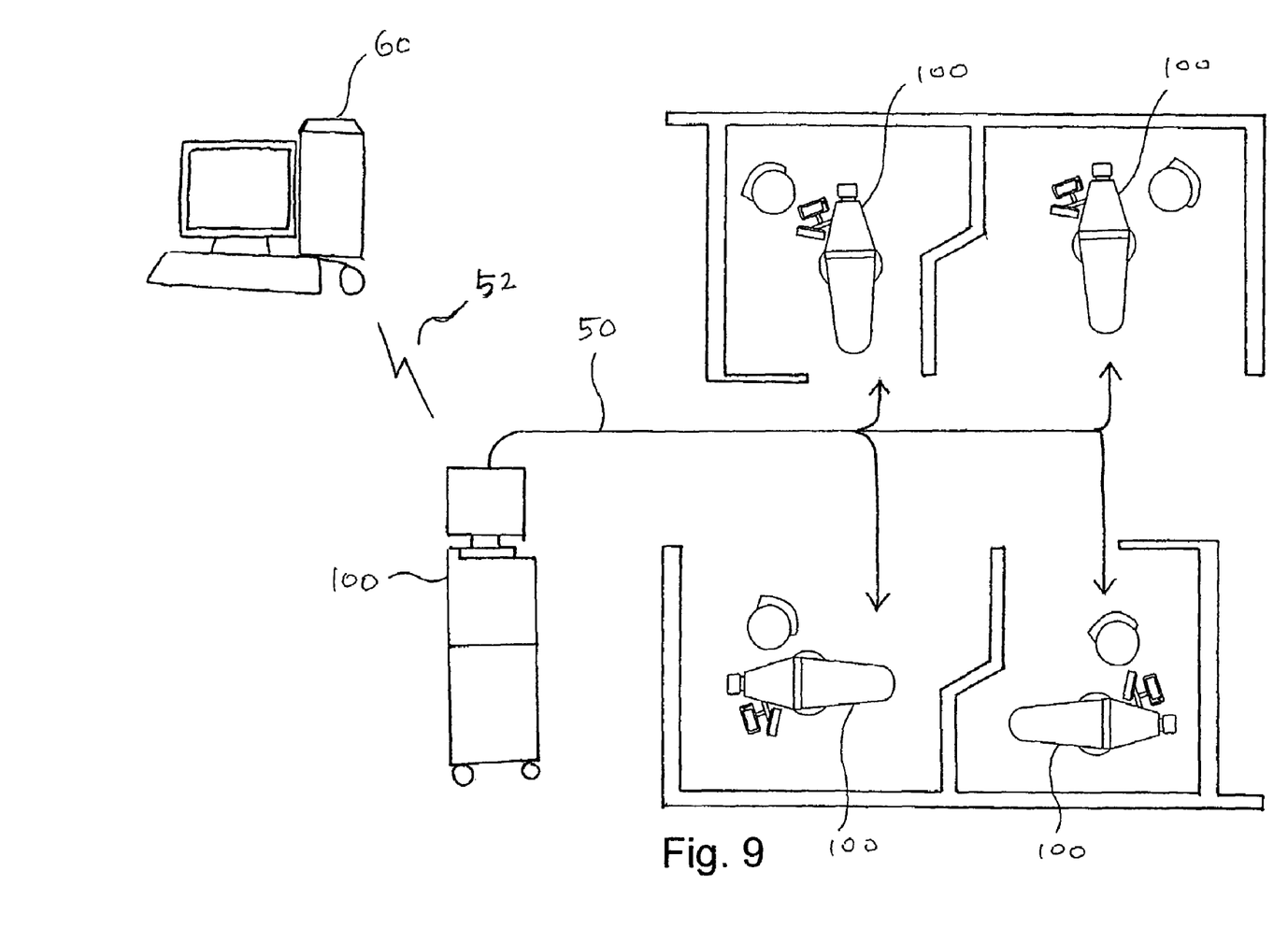
FIG. 9 is a schematic diagram showing a network of the digital surgical scope.
Figure 10:
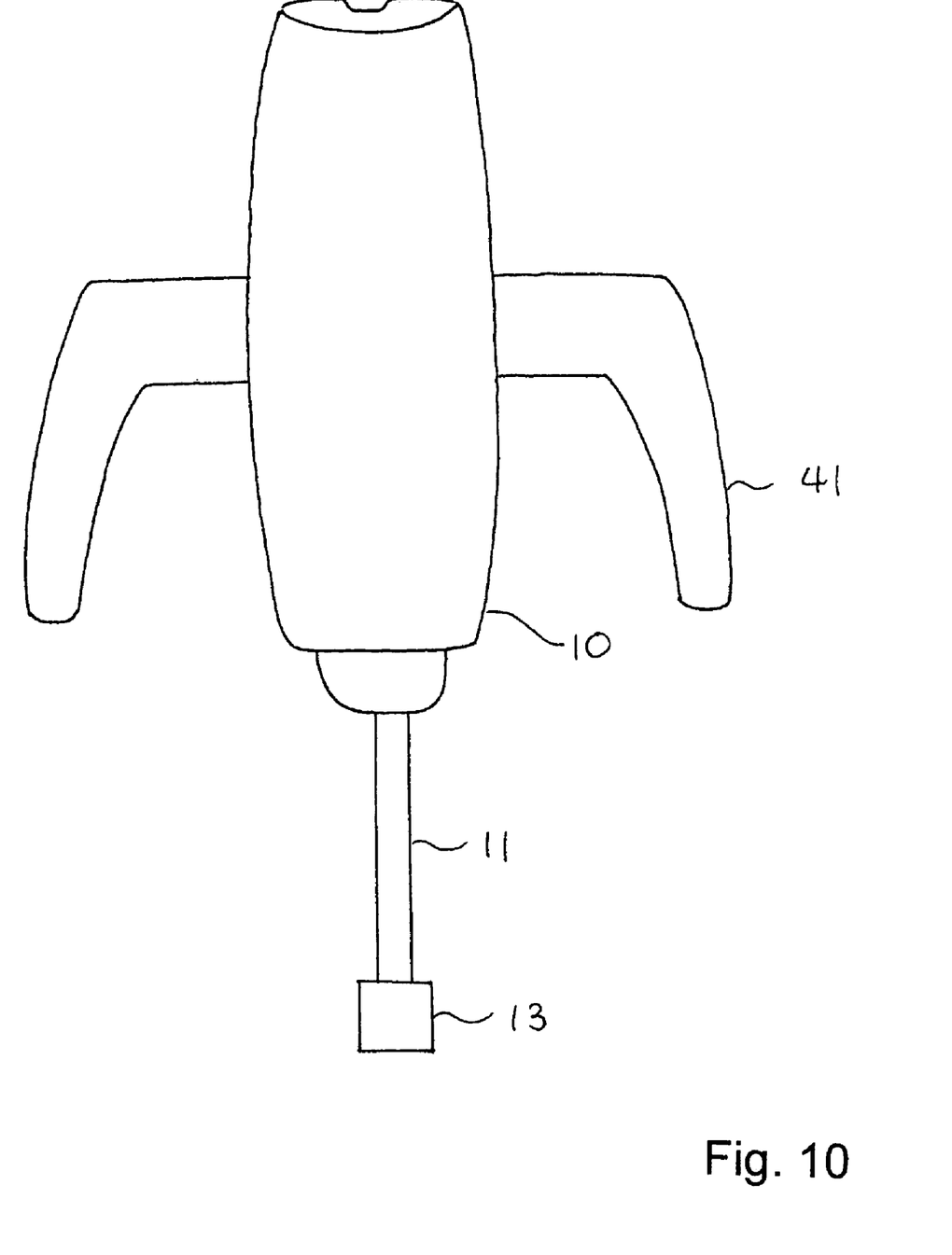
FIG. 10 is a front elevation view of the digital surgical scope with a detachable mirror.
Figure 11:
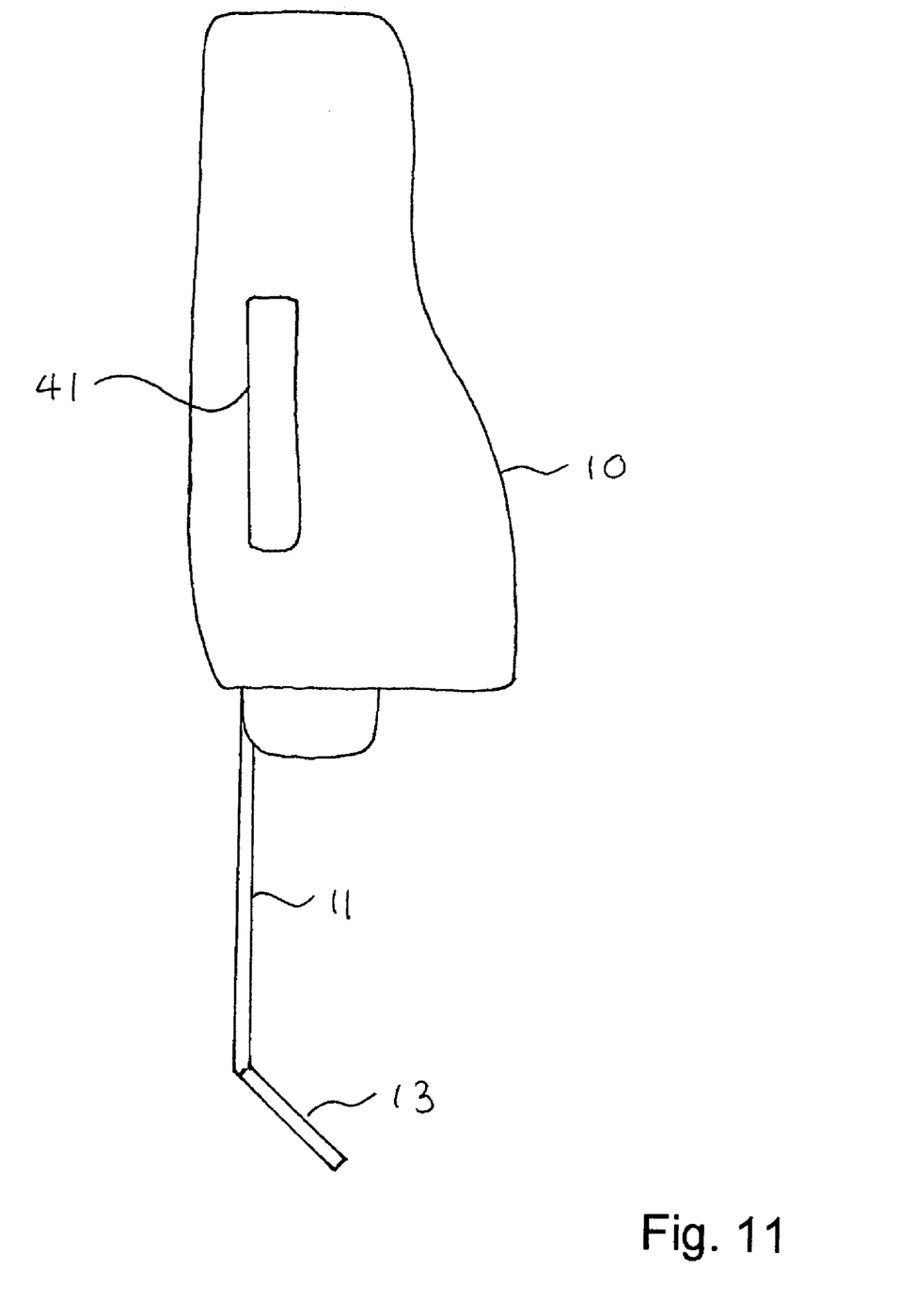
FIG. 11 is a side elevation view of the digital surgical scope with a detachable mirror.

As shown in FIG. 9, the system 100 further includes a plurality of digital surgical scopes 10, a communication network 50 and one or more controls 32 for controlling the behavior of the image data processing/storing device 30, and a detachable mirror or reflecting material such as prism 13 disposed on a extended bar 11 from the digital surgical scope 10 for reflecting images from the inside of mouth to the digital surgical scope 10 (refer to FIG. 10 and FIG. 11). The detachable mirror 13 is for reflecting the image of the hidden inside of mouth into the digital surgical scope. The control 32 includes a button, a pedal, and a lever as shown in FIG. 1. The method S1000 further includes steps of displaying the images on one or more remote displays 60 and streaming and broadcasting the images and videos through the communication network 50 via internet, and controlling the behavior of the image data taking device 12 and the image data processing/storing device 30 with the controls as shown in FIG. 9.

The image data taking device 12 includes a charge coupled device (CCD) or a complementary metal-oxide-semiconductor (CMOS). The image data processing/storing device 30 includes a computer and an image capturing/storing device.

The in-line illumination device 16 includes a light source 19, and a beam splitter 18, and the light source 19 includes a fiber optic device 17 and emits light parallel to the optical axis 91 of the microscope 10.

The mirror or prism 15 changes the direction of the light from the light source 19 by ninety (90) degrees. Also, the light source 19 may emit directly to the beam splitter 18 without a mirror or prism 15. The beam splitter 18 is disposed in the optical axis 91 of the microscope with forty five (45)-angles to the optical axis 91, and reflects the light from the mirror or prism 15 to the object 90 and allows the light from the object 90 to the lens assembly 14 of the microscope 10 to pass.

The digital surgical scope 10 has an adjustable magnification up to one hundred twenty (120) times including optical and digital zoom.

The method S1000 further includes steps of creating a database of information on a new patient S1018 and searching information or an exam history on a predetermined old patient from the database S1016 as in FIG. 2.

Alternatively, a dental microscopic procedure, using a digital surgical scope 100, includes steps for a) creating an entry in the database for a new patient (S1012); b) selecting a predetermined patient and retrieving the related information from the database (S1016); c) displaying the retrieved information(S1014); d) creating a new exam for the patient (S1018); e) opening the exam history and selecting an exam of the patient (S1024); f) capturing images (S1022); g) enhancing images (S1026); h) browsing a history of the patient (S1028); and i) selecting and performing functions on the images (S1032). The function includes deleting, exporting, importing, multi-viewing, printing, and managing the images with the database as shown in FIG. 2.

The step (S1100) of capturing images includes steps of c1) adjusting live image quality by adjusting the camera controls, white balance, RGB color gamma value, viewing area, zoom in, zoom out, and full screen, wherein the camera control includes gain, offset, and exposure (S1102); c2) viewing the adjusted live image (S1104); c3) capturing a snapshot image and a video clip (S1106); c4) controlling the capturing with a foot pedal or a button (S1110); c5) replaying the captured image or video (S1120); and c6) viewing details of the image or video (S1122) by selecting functions of deleting, saving, and refreshing (S1124) as shown in FIG. 3.

The step of enhancing images (S1200) includes steps of e1) adjusting the image quality by controlling brightness, contrast, edge enhancement, and histogram contrast (S1202); e2) analyzing the images to manipulate the image to rotate, zoom in, zoom out, pan, magnify, and measure geometrical dimension, and the geometrical dimension includes angles, lengths, distances between two points (S1208); and e3) annotating the image for adding text and geometrical objects, and the geometrical objects includes lines and shapes (S1212).

The step of browsing the history of patient (S1300) includes steps of b1) showing all images in thumbnail format (S1308); b2) showing the digital surgical microscope image and X-ray images (S1310); b3) showing the comparison of the digital surgical microscope image and the X-ray image (S1312); b4) comparing images by selecting multiple images and multi-viewing (S1320); and b5) presenting a case for patient by selecting multiple images to present a possible treatment plan or treatment result from previous problems (S1332).

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed:

1. A dental microscopic procedure, using a digital surgical scope comprising:
    1) a digital surgical scope comprising a microscope lens assembly for magnifying an optical image of an object and an in-line illumination device for illuminating the object along the same optical axis and from the same direction of the microscope lens assembly;
    2) an image data taking device;
    3) an image data processing and storing device for manipulating the image taken by the microscope lens assembly and the image data taking device, wherein the image data processing and storing device comprises a database; and
    4) one or more displays for displaying the image from the image data processing device, comprising steps for:
    a) creating an entry in the database for a new patient;
    b) selecting a predetermined patient and retrieving the related information from the database;
    c) displaying the retrieved information;
    d) creating a new exam for the patient;
    e) opening the exam history and selecting an exam of the patient;
    f) capturing images;
    g) enhancing images;
    h) browsing a history of the patient; and
    i) selecting and performing functions on the images, wherein the function comprises deleting, exporting, importing, multi-viewing, printing, and managing the images with the database, wherein the step of capturing images comprises steps of:
    f1) adjusting live image quality by adjusting the camera controls, white balance, RGB color gamma value, viewing area, zoom in, zoom out, and full screen, wherein the camera control comprises gain, offset, and exposure;
    f2) viewing the adjusted live image;
    f3) capturing a snapshot image and a video clip;
    f4) controlling the capturing with a foot pedal or a button;
    f5) replaying the captured image or video; and
    f6) viewing details of the image or video by selecting functions of deleting, saving, and refreshing, wherein the step of enhancing images comprises steps of:
    g1) adjusting the image quality by controlling brightness, contrast, edge enhancement, and histogram contrast;
    g2) analyzing the images to manipulate the image to rotate, zoom in, zoom out, pan, magnify, and measure geometrical dimension, wherein the geometrical dimension comprises angles, lengths, distances between two points; and
    g3) annotating the image for adding text and geometrical objects, wherein the geometrical objects comprises lines and shapes, wherein the process of browsing the history of patient comprises of:
    h1) showing all images in thumbnail format;
    h2) showing the digital surgical microscope image and X-ray images;
    h3) showing the comparison of the digital surgical microscope image and the X-ray image;
    h4) comparing images by selecting multiple images and multi-viewing; and
    h5) presenting a case for patient by selecting multiple images to present a possible treatment plan or treatment result from previous problems.

* * * * *